United States Patent
Najarian et al.

(10) Patent No.: US 11,531,851 B2
(45) Date of Patent: Dec. 20, 2022

(54) SEQUENTIAL MINIMAL OPTIMIZATION ALGORITHM FOR LEARNING USING PARTIALLY AVAILABLE PRIVILEGED INFORMATION

(71) Applicant: THE REGENTS OF THE UNIVERSITY OF MICHIGAN, Ann Arbor, MI (US)

(72) Inventors: Kayvan Najarian, Northville, MI (US); Jonathan Gryak, Ann Arbor, MI (US); Elyas Sabeti, Ypsilanti, MI (US); Joshua Drews, Ann Arbor, MI (US)

(73) Assignee: THE REGENTS OF THE UNIVERSITY OF MICHIGAN, Ann Arbor, MI (US)

( * ) Notice: Subject to any disclaimer, the term of this patent is extended or adjusted under 35 U.S.C. 154(b) by 252 days.

(21) Appl. No.: 16/782,573

(22) Filed: Feb. 5, 2020

(65) Prior Publication Data

US 2020/0250496 A1 Aug. 6, 2020

Related U.S. Application Data

(60) Provisional application No. 62/801,426, filed on Feb. 5, 2019.

(51) Int. Cl.
*G06K 9/62* (2022.01)
*G16H 50/50* (2018.01)
*G06N 20/10* (2019.01)

(52) U.S. Cl.
CPC ......... *G06K 9/6269* (2013.01); *G06K 9/6256* (2013.01); *G06K 9/6286* (2013.01); *G06N 20/10* (2019.01); *G16H 50/50* (2018.01)

(58) Field of Classification Search
CPC .. G06K 9/6269; G06K 9/6286; G06K 9/6256; G06K 9/6262; G16H 50/50; G16H 50/20; G06N 20/10
See application file for complete search history.

(56) References Cited

U.S. PATENT DOCUMENTS

| | | |
|---|---|---|
| 5,649,068 A | 7/1997 | Boser et al. |
| 5,950,146 A | 9/1999 | Vapnik |
| 7,979,367 B2 | 7/2011 | Izmailov et al. |
| 8,065,241 B2 | 11/2011 | Vapnik et al. |
| 8,135,652 B2 | 3/2012 | Graf et al. |
| 8,315,956 B2 | 11/2012 | Vashist et al. |
| 9,569,401 B2 | 2/2017 | Pechyony et al. |
| 2006/0112026 A1 | 5/2006 | Graf et al. |

(Continued)

OTHER PUBLICATIONS

Deep LPIU, Lambert et al, 2018; https://arxiv.org/pdf/1805.11614.pdf (Year: 2018).*

(Continued)

*Primary Examiner* — Jianxun Yang
(74) *Attorney, Agent, or Firm* — Marshall, Gerstein & Borun LLP (57) ABSTRACT

Computational algorithms integrate and analyze data to consider multiple interdependent, heterogeneous sources and forms of patient data, and using a classification model, provide new learning paradigms, including privileged learning and learning with uncertain clinical data, to determine patient status for conditions such as acute respiratory distress syndrome (ARDS) or non-ARDS.

11 Claims, 7 Drawing Sheets

(56) References Cited

U.S. PATENT DOCUMENTS

2008/0089846 A1* 4/2008 Driehuys ............. G01R 33/483
424/9.3
2010/0017356 A1* 1/2010 Degrave ............ G01N 30/8675
706/54
2019/0370387 A1* 12/2019 Cao ........................ G16H 10/60

OTHER PUBLICATIONS

Pechyony et al., "Smo-style algorithms for learning using privileged information," DMIN 235-241 (2010).
Pechyony et al., "Fast optimization algorithms for solving svm+", Stat. Learning and Data Science, 1 (2011).
Vapnik et al., "A new learning paradigm: Learning using privileged information," Neural Networks 22(5-6):544-557 (2009).

* cited by examiner

SEQUENTIAL MINIMAL OPTIMIZATION ALGORITHM FOR LEARNING USING PARTIALLY AVAILABLE PRIVILEGED INFORMATION

CROSS-REFERENCE TO RELATED APPLICATIONS

This application claims the benefit of U.S. Provisional Application Ser. No. 62/801,426, filed Feb. 5, 2019, the entirety of which is hereby incorporated herein by reference.

STATEMENT REGARDING FEDERALLY SPONSORED RESEARCH OR DEVELOPMENT

This invention was made with government support under IIS1722801 awarded by the National Science Foundation. The government has certain rights in the invention.

FIELD OF THE DISCLOSURE

The present disclosure relates generally to techniques for supervised machine learning and, more particularly, to techniques for improving model performance by simultaneous incorporation of partially available privileged information and label uncertainty.

BACKGROUND

The background description provided herein is for the purpose of generally presenting the context of the disclosure. Work of the presently named inventor, to the extent it is described in this background section, as well as aspects of the description that may not otherwise qualify as prior art at the time of filing, are neither expressly nor impliedly admitted as prior art against the present disclosure.

The digitization of health data provides an important opportunity for new knowledge discovery and improved care delivery, through the development of electronic analytics and clinical decision support systems (CDSS) that leverage vast data to support increasing aspects of healthcare. By synthesizing digital information into actionable knowledge, these systems have the potential to provide important insights into the health status of patients, helping physicians make more timely and accurate medical diagnosis and evidence-based treatment decisions. Yet, in modern settings, providers are inundated by the vast amounts of clinical data being generated during routine patient care. CDSS that can integrate these disparate data sources (structured and unstructured) in real-time and effectively assist clinicians in medical decisions show promise for transforming how patient care is delivered. These systems could support precision medicine by improving rapid and accurate diagnosis and make just-in-time treatment recommendations that improve care quality and clinical outcomes.

An example medical condition that could benefit from a clinical application of CDSS is in acute respiratory distress syndrome (ARDS) care. ARDS is a fulminant inflammatory lung injury that is the downstream consequence of critical illnesses such as sepsis, pneumonia, or trauma, evolving over hours to days. When diagnosed early, multiple evidence-based management strategies can be provided to patients with ARDS that improve clinical outcomes. However, more than half of patients with ARDS are not immediately recognized by practicing clinicians and, as a consequence, fail to receive these life-saving treatments. Patients who develop ARDS first present with serious illnesses including sepsis, pneumonia or traumatic injury. As their illness evolves, massive streams of clinical data are collected from their bedside monitoring devices and recorded in electronic health records as part of routine care. These data are asynchronous, with varying temporal frequency (from millisecond to daily) and stored in varying formats. Within 24-72 hours after presentation, some patients progress and develop ARDS. However, some clinicians may fail to recognize ARDS if they are unable to synthesize the clinical data, recognize this evolution and obtain and correctly interpret chest imaging and make an ARDS diagnosis.

The inability of healthcare providers to process the massive data-streams generated during the care of critically ill patients has been specifically cited as a potential reason for ARDS misdiagnosis. Delay in recognition of this condition, followed by delay in the institution of appropriate treatment is associated with increased mortality. Yet, only after a healthcare provider correctly interprets a chest x-ray and synthesize this information with other clinical data will they correctly diagnosis ARDS. There is a need for a CDSS that models the diagnostic process, such that the accuracy and reliability of ARDS diagnosis can be greatly enhanced, thereby ensuring patients receive timely treatments that improve clinical outcomes.

The example of ARDS demonstrates many of the challenges facing designers of CDSS and other systems that are called upon to assess large amounts of data, that is, big data analytics systems for personalized medicine and other personalized applications.

Identifying relevant clinical information from massive data streams is one major challenge. In many healthcare settings, for example, there is an abundance of rich, continuously measured data collected thorough all stages of care. However, there is a lack of reliable systems to: 1) extract clinically relevant features from these data; and 2) integrate these features with clinical data to provide quantitative predictions/recommendations about patient's health status, thereby assisting clinicians to improve the quality of decision making. In case of ARDS, for example, patients at risk for ARDS are typically monitored with continuous electrocardiogram (ECG) and photoplethysmography (PPG) in the form of pulse oximetry, in addition to discrete laboratory and vital sign data. Potential patterns in these signals that could signify developing respiratory insufficiency and ARDS are not extracted or used in real-time decision making.

Another challenge is having a system exhibiting robustness to uncertainty, a particular issue for health data. For the diagnosis of ARDS, as well as many other clinical diseases and syndromes, medical experts can confidently label a subset of patients as "positive" and "negative." However, there may also be many cases, particularly at the early stages of diagnosis, where even medical experts may have far less confidence in labeling patients. Computational models that can account for this uncertainty may be more robust to the use of noisy or incomplete health data for medical diagnosis.

Another challenge is the potential for using data that is unavailable in live clinical environments, but available in training phase. In a conventional treatment flow for a patient, a chest radiograph is the main confirmatory data necessary for a definitive diagnosis of ARDS. Patients known to have early evidence of lung injury on chest x-ray are at high risk for progression to ARDS. However, a chest radiograph may not always be available in real-time, and even the need to perform a chest radiograph may not be recognized at early stages. In addition, the frequency at which chest radiographs are obtained is variable and not amendable to high density collection, in contrast to physiologic monitoring data. Therefore, ideally a clinical decision support system would not rely on chest radiographic data to determine a patient's ARDS risk. However, chest radiographs still can provide critical information about a patient's current state of illness, and this information may be of great value during retrospective training of algorithms that can detect high risk patients.

Another challenge is the availability of reliable methods for interpreting medical data, such as chest x-ray interpretation. At the time that a chest x-ray is made available, radiology interpretation plays the major role in diagnosis of ARDS. However, due to the noisy nature of these images, the expertise of the interpreter, and other factors, the reliability of chest radiograph interpretation for ARDS is low among clinicians. There is a clear need for image processing algorithms to quantitatively express and extract the changes in the chest x-rays (compared to normal cases) and evaluate the presence and severity of ARDS.

Another challenge is how to incorporate cognitive/behavioral data. While the importance and significance of cognitive and behavioral data have been recognized by the healthcare community, its use has not been realized in CDSSs. There is a need for decision support system capable of resolving these short comings and, in particular, for clinical decision support systems capable of utilizing cognitive and behavioral data collected upon patient presentation and capable of integrating this data with all other clinical data to improve characterization of patient's health status.

SUMMARY OF THE INVENTION

In examples, the present techniques provide systems having advanced computational algorithms to integrate and analyze data to consider multiple interdependent, heterogeneous sources and forms of patient data. In some examples, these systems leverage longitudinal clinical data for early disease detection. For example, clinical diagnosis may be achieved using a classification model that determines a patient's status (e.g., ARDS or non-ARDS) based on a set of clinical features. Classifying patients at time points prior to their development of a condition, time points after development, and tracking illness recovery, are important for informing treatment decisions—tasks less easily addressed using time-to-event models.

Using a classification model, the present techniques introduce new learning paradigms, including privileged learning and learning with uncertain clinical data. A known issue with classification systems is that observations on individual patients over time can be correlated, breaking the assumption of independence necessary for standard statistical inference. Some have proposed model autocorrelation in longitudinal patient data explicitly. In examples herein, systems deploy a sampling strategy when building datasets for training machine-learning algorithms that limits the number of highly correlated observations within individual patients to limit overfitting.

In examples, the present techniques use a classification model with uncertainty in training labels. Datasets in many applications may have uncertainty in their training labels or the input data (i.e. features) might be corrupted. For instance, in medical applications, precisely determining the prognosis of patients might be difficult as patients might not describe what has happened to them or how they feel, results of the laboratories might be erroneous and so on. In examples, the present techniques provide a support vector machine (SVM) based approach with embedded uncertainty in training labels.

In examples, the present techniques use privileged information to improve and tune classification models during training. For example, training is implemented using a learning paradigm in which the learner is provided with not only a set of training examples, but also a set of additional "privileged information" that can help significantly improve the learning process. Learning using privileged information (LUPI) considers the fact that while privileged information may not be available at the testing stage, the abundance of such information in the training phase can help tune and improve classification models. Various sources of privileged information can be found in healthcare applications, for example, including in retrospective databases and not just real-time environments. Example privileged information include (i) physiological waveform signals (e.g., Electrocardiogram (ECG), Arterial Blood Pressure (ABP), pulse oximetry using photoplethysmography (PPG), and respiratory rate (RR)), (ii) clinical/demographic data (e.g., electronic medical records (EMR) data such as chief complaint, medications, comorbidities, age, gender, injury scores, respiratory support (i.e. ventilator support) and laboratory results), (iii) medical imaging data (e.g., chest image data for ARDS diagnosis applications), (iv) cognitive and behavioral data (e.g., Glasgow Coma Scale (GCS) data, level of orientation, motor strength, pronator drift, arousal, speech and behavior observations and pain rating, and composite scores including the confusion assessment method (CAM) and Richmond Agitation Sedation Scale (RASS)), and (v) expert adjudicated patient outcomes (e.g., healthcare professional reviews of hospitalizations of other patients with diagnosed conditions such as ARDS onset, healthcare professionals rating of their confidence in assessments to capture clinical uncertainty, healthcare professional annotations, etc.)

Learning using privileged information is highly useful for time-course predictive scenarios such as clinical decisions making, in which the retrospectively training data sets contain highly informative additional information that cannot be used by conventional machine learning. For example, in the case of the early detection and prediction of ARDS, while the conventional machine learning would only consider the features extracted from clinical/physiological data for early detection of ARDS, i.e., the present techniques can consider the available data, along with the chest x-rays that are not available at the time of the actual decision making. In other words, since the chest x-rays are available in the training datasets, they can serve as the privileged information when creating the classification models that map the clinical/physiological data to the presence or absence of ARDS, i.e., an $\{-1, 1\}$ determination. Indeed, in some examples, the present techniques apply the formulation of LUPI for SVM, generating new, optimized SVM techniques that shows superior results to previous SVM techniques.

In examples, the present techniques integrate streaming clinical data to detect ARDS by tracking evolving cardiovascular and respiratory system physiology in real-time, before any chest x-ray is ordered. The present techniques can then recommend a chest radiograph when a patient's ARDS risk reaches a specific threshold for further evaluation of possible developing ARDS. The present techniques can then automatically analyze the radiograph for features consistent with developing ARDS and incorporate these additional features into the machine-learning algorithm to then make an updated clinical diagnosis of ARDS.

In an example, a computer-implemented method of developing a classifier model for identifying a medical condition of a subject, the method comprises: receiving training data for a plurality of subjects, where the training includes sensed physiological data, imaging data, demographic data, and/or other clinical data, where at least some of the training data is for subjects having the medical condition and at least some of the training data is for subjects not having the medical condition, wherein the training data includes privileged information where at least a portion of the privileged information is label uncertain privileged information; identifying the label uncertain privileged information; applying a penalty parameter to each label uncertain privileged information, wherein the penalty parameter establishes a soft-margin decisional boundary for the label uncertain privileged information; performing an optimization on (i) the label uncertain privileged information having the penalty parameters, (ii) the privileged information in the training data that has certain labels, and (iii) non-privileged information in training data, to develop a mapping to an outcome determination of the medical condition; and generating a classifier model based on the mapping to classify testing data as corresponding to the presence of the medical condition or to the absence of the medical condition.

In some examples, the computer-implemented method includes applying the training data to a support vector machine (SVM) framework configured to map training data to a vector space and generate a decision hyperplane classifier model for identifying the presence of the medical condition and for identifying the absence of the medical condition.

In some examples, the computer-implemented method includes configuring the support vector machine (SVM) framework to map privileged information in the training data and non-privileged information in the training data to the vector space for generating the decision hyperplane classifier model.

BRIEF DESCRIPTION OF THE DRAWINGS

For a more complete understanding of the disclosure, reference should be made to the following detailed description and accompanying drawing figures, in which like reference numerals identify like elements in the figures, and in which.

DETAILED DESCRIPTION

The present techniques include enhanced machine learning systems implemented with a learning using privileged information configuration. The supervised learning system is able to access, analyze, and use privileged information available for training data, which is not available for test data. The supervised learning systems herein are able to learn where privileged information is known for all the training data or for all part of the training data. The later example of learning using partially available privileged information may be implemented in numerous ways. In some examples, a supervised learning system implements modified support vector machine (SVM) techniques to implement such learning. In some examples, a supervised learning system combines a sequential minimal optimization (SMO) process with the SVM to implement such learning.

Figure 1A:
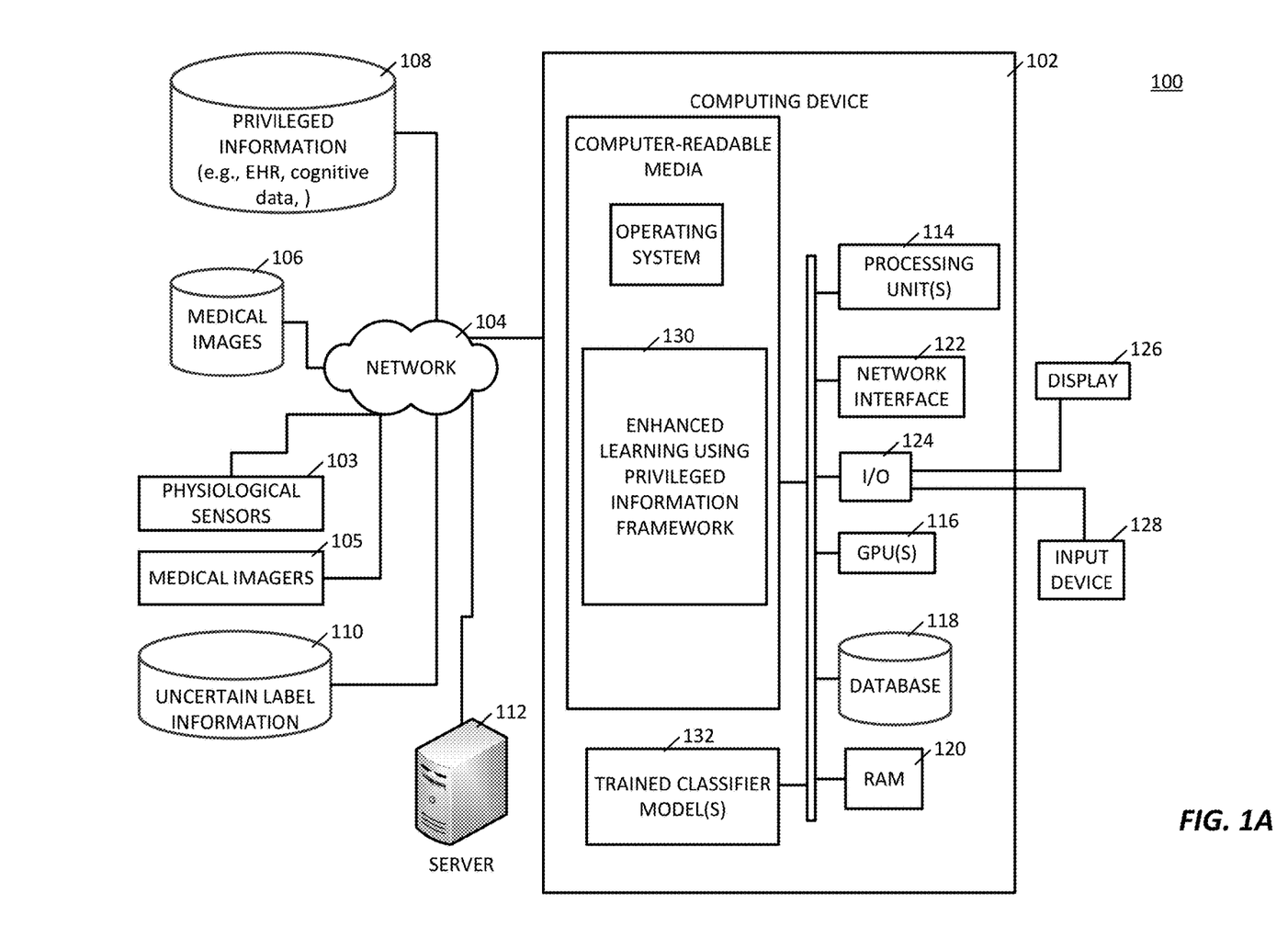
FIG. 1A illustrates an enhanced learning using privileged information system, in accordance with an example herein.

FIG. 1A illustrates an example learning using privileged information system 100, in accordance with examples herein. A computing device 102 implementing an enhanced learning using privileged information framework is coupled to a network 104 for receiving various types of data, for training one or more classifiers model and for executing the trained classifier models on testing data, e.g., during treatment of a patient. The network 104 may be a wireless or wired network communicating with physiological sensors 103 and medical imagers 105 generating real time data on a patient. The network 104 may also be connected to databases, including a medical images database 106 which may be used for specific applications such as ARDS detection, privileged information databases 108 such as electronic health records databases and cognitive health databases. This database may include partially privileged information, as well. The network 104 may be further connected to uncertain labeled information databases 110, which may include privileged information with uncertain labeling. As further shown, the network 104 may be connected to a network accessible server 112 that may store data from any of the foregoing connected devices or other data that may be used for training and/or testing using the computing device.

The computing device 102 includes one or more processing units 114, one or more optional graphics processing units 116, a local database 118, random access memory 120, a network interface 122, and Input/Output (I/O) interfaces 124 connecting the computing device 102 to a display 126 and user input device 128.

The various enhanced learning using privileged information described herein, including as applied to SVM, is achieved using the enhanced learning using privileged information framework 130, which generates one or more trained classifier models 132 also stored in the computing device 102.

Figure 1B:
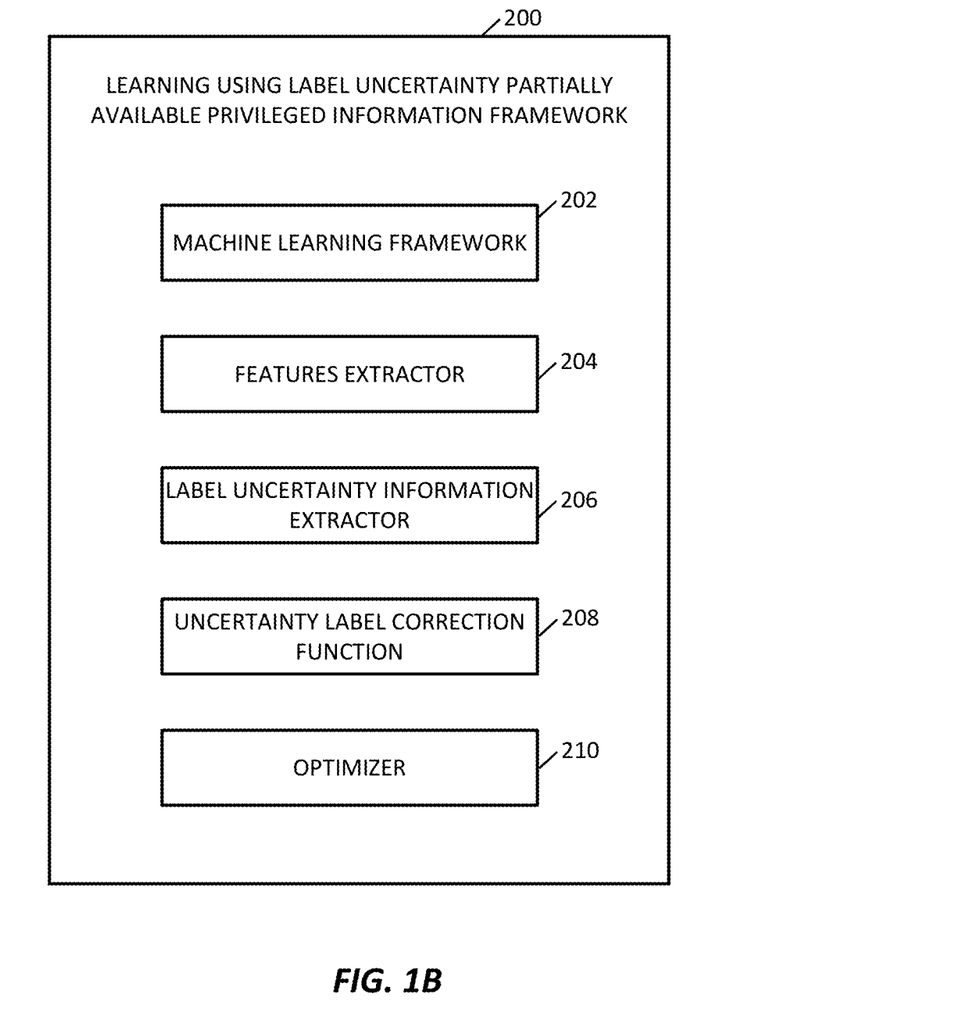
FIG. 1B is a block diagram of an example implementation of the enhanced learning using privileged information framework of FIG. 1B, in accordance with an example.

FIG. 1B illustrates an example of the enhanced learning using privileged information framework 130. In the illustrated example, framework 200 is implemented as a learning using label uncertainty partially available privileged information framework. The framework includes a machine learning framework 202 that may store any of a variety of types of machine learning techniques. In examples described below, this framework is an SVM, although other machine learning techniques may be used. A features extractor 204 receives the data over the network and extracts features from that data, features such as physiological features, waveforms, image features, etc. The features extraction may further extract demographic information and other EHR data to be used in constructing a classifier model. A label uncertainty information extractor 206 identifies particular types of data, specifically data that has uncertain labeling. This data may be privileged information or partially privileged information for example. An uncertainty label correction function 208 takes the identified label uncertainty information and applies a correction function to minimize weighting of such information during training of the classifier model. The correction function may still maintain the extracted information but seeks to optimize that information for use in machine learning. An optimizer 210 is used to optimize the correction function process, for example, in an iterative process, such that the label uncertain information is appropriately weighted over success iterations of the process.

Figure 2:
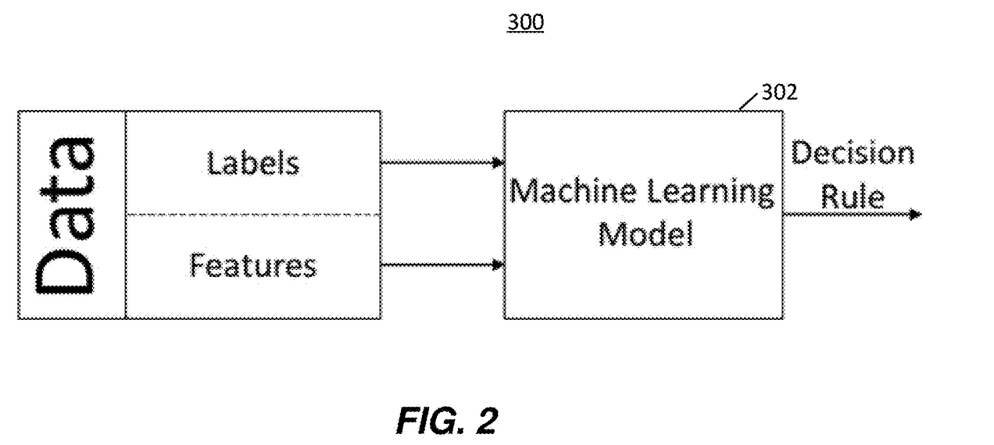
FIG. 2 illustrates a schematic of a conventional machine learning model, implemented as a support vector machine.

FIG. 2 illustrates the schematic a conventional machine learning model 300, such as an SVM, that may be used in a clinical decision support systems (CDSS) to assist in monitoring for and diagnosing a medical condition of a subject. Initial medical data is obtained from the subject, at the time of care. For example, diagnostic data such as demographics, medical history, medications, and laboratory results may be obtained. That medical data may be characterized by having labels that are created by a clinician who is a domain expert for the medical condition under consideration, and features that may include all available medical data, a subset of medical data as deemed salient by a domain expert, summary statistics of the medical data, or some combination thereof. In the illustrated example, the CDSSS is implemented using a machine learning model 302 that applies one or more trained decision rules designed to assess the medication condition. That assessment may be a binary diagnostic assessment, such as the subject has a condition or does not have a condition. That assessment may be a probabilistic assessment of the likelihood the subject has that condition. In an example that uses an SVM as the machine learning model the decision rule may be the decision function $f(z) = w \cdot z + b$.

In a classical SVM algorithm, given a set of training data $(x_1, y_1), \ldots, (x_n, y_n)$, with $x_i \in X, y_i \in \{-1, 1\}$, the SVM first maps training data vector $x \in X$ into vector (space) $z \in Z$, and the SVM constructs the optimal separating hyperplane by learning the decision rule $f(z) = w \cdot z + b$, where w and b are hyperplane parameters and the solution of $$\min_{w,b,\xi_1} \frac{1}{2}\|w\|_2^2 + C\sum_{i=1}^{n} \xi_i$$

such that $\forall 1 \leq i \leq n$, $y_i(w \cdot z_i + b) \geq 1 - \xi_i$ and $\forall 1 \leq i \leq n$, $\xi_i > 0$, where $C > 0$ is a hyperparameter.

In some examples, herein, this conventional SVM is extended to include learning using privileged information. In a learning using privileged information (LUPI) paradigm, in addition to the standard training data, $x_i \in X$, $y_i \in \{-1, 1\}$, the machine learning model of FIG. 2 is provided with privileged information. This privileged information, $x^* \in X^*$, may only be available for training data and not available for testing data collected from the subject at the time of care. In such example, the present techniques rely upon a triplet of data, e.g., $(x_i, x_i^*, y_i)$, for training. With such a modification to SVM, in addition to mapping data vector $x \in X$ into vector (space) $z \in Z$, the modified SVM is configured to map privileged information $x^* \in X^*$ into vector (space) $z^* \in Z^*$, and then the slack variable $\xi_i$ of SVM may be replaced by the correcting function $\varphi(z^*) = w^* \cdot z^* + b^*$.

Generally speaking, privileged information is any information that is readily available during the training phase of machine learning not necessarily available during the testing phase, with the potential to improve model performance. Privileged information can be periodic data such as the timed polling of a measured condition or scheduled release of financial reports, structural information such as the topological structure of a protein, effectively static data such as clinical/demographic information or tax rates, time-series data such as physiological waveforms or equity pricing, image data, and outcome data including expert adjudicated patient data or corporate profits. Privileged information can be measured data or coded data, obtained from local connected medical equipment, databases from remote connected sources, market research companies and governmental agencies.

In an example of learning using privileged information, the assumption is that privileged information is available for all the training data. However, this is not always the case. In many practical applications, privileged information is only available for fraction of training data.

Therefore, in some examples, the supervised learning systems herein are configured to learn using partially available privileged information (also termed herein "LUPAPI") techniques, in which the training data is provided with m triplets, $(x_i, x_i^*, y_i)$, of samples with privileged information and n-m pairs $(x_i, y_i)$ of samples without privileged information. These LUPAPI techniques may be applied to SVM, using a SMO-based approach, for example.

In some examples, supervised learning systems herein are configured to compensate for another condition in training, label uncertainty, that is the lack of confidence in labels for training data. Label uncertainty is very significant in medical data, since there is always lack of consensus between clinicians in their diagnosis. In some examples, supervised learning systems herein are configured to incorporate the label uncertainty into the LUPAPI techniques by allowing variability in parameters through training samples based on label confidence. For example, a slack variable (or correcting function) may be used that permits misclassification with penalty parameter to establish soft-margin decision boundaries. In this way, data with high label confidence can be given more weight and influence on the decision boundary in comparison to data with lower label confidence. We term supervised learning systems with this modification as configured with learning using label uncertainty partially available privileged information ("LULUPAPI").

Figure 3:
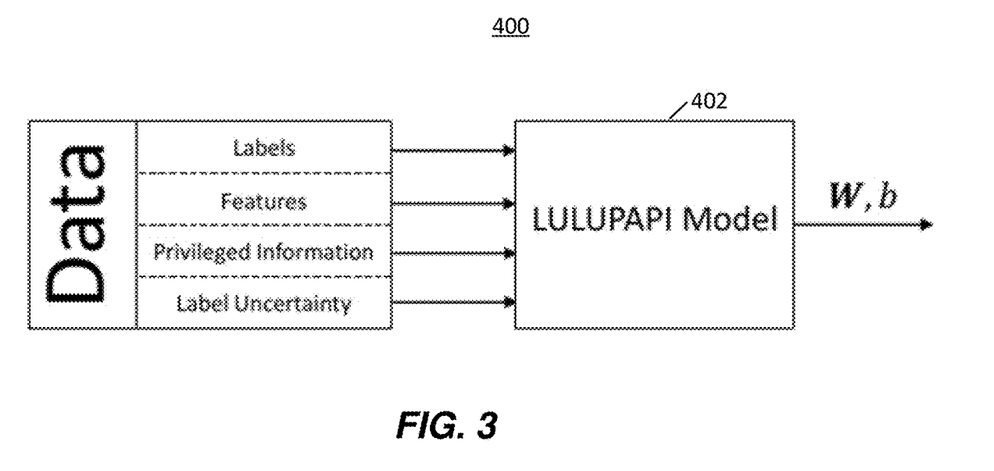
FIG. 3 illustrates a schematic of an enhanced machine learning model, in accordance with the present techniques.

FIG. 3. Illustrates an example supervised learning system having a LULUPAPI configuration 400. Collected data includes labels and features, as with conventional systems such as that of FIG. 2. However, additional data for a subject is collected, including privileged information and label uncertainty information. All of this data is provided to an enhanced machine learning model 402 that generates a decision model, which in the illustrated example are hyperplane parameters, w, b, of an SVM decision model.

In some example implementations of the LULUPAPI approaches herein, compensating for label uncertainty, using training samples according to:

$(x_1, x_1^*, y_1, \pi_1), \ldots, (x_m, x_m^*, y_m, \pi_m), (x_{m+1}, y_{m+1}, \pi_{m+1}), (x_{m+2}, y_{m+2}, \pi_{m+2}), \ldots, (x_n, y_n, \pi_n)$ $x_i \in X, x_i^* \in X^*, y_i \in \{-1, 1\}, \pi_i \in \mathbb{R}$ where $\pi_i$ is quantitative measure of uncertainty in the labels (see FIG. 3).

In various examples, a supervised learning system consider is implemented using any of a number of different LULUPAPI configurations.

In a first LULUPAPI configuration, a supervised learning system applies a correcting function for data with privileged information and slack variable for data without privileged information. In such examples, the supervised learning system determines the decision rule and the correcting function hyperplane parameters through simultaneous optimization of:

$$\min_{w,b,w^*,b^*,\xi} \frac{1}{2}\|w\|_2^2 + \frac{\gamma}{2}\|w^*\|_2^2 + C\sum_{i=m+1}^{n}\pi_i\xi_i + C^*\sum_{i=1}^{m}(w^*\cdot z_i^* + b^*) \quad (2)$$

$$\text{s.t. } \forall\, 1\le i\le m \quad y_i(w\cdot z_i + b) \ge 1 - (w^*\cdot z_i^* + b^*)$$
$$\forall\, 1\le i\le m \quad w^*\cdot z_i^* + b^* \ge 0$$
$$\forall\, m+1\le i\le n \quad y_i(w\cdot z_i + b) \ge 1 - \xi_i$$
$$\forall\, m+1\le i\le n \quad \xi_i \ge 0$$

where $C>0$, $C^*>0$, and $\gamma>0$ are hyperparameters. In this formulation, the term $\gamma\|w^*\|_2^2$ is intended to restrict the VC-dimension of the function space. The slack variables and the label uncertainty may only be used for training data without privileged information. During testing, labels may be determined by the decision rule.

In another example LULUPAPI configuration, a supervised learning system may, for data with privileged information, replace slack variables with a smooth correcting function $\varphi(z^*)=w^*\cdot z^*+b^*$ or the supervised learning system may use a mixture of slacks as $\xi'_i=(w^*\cdot z_i^*+b^*)+\rho\xi^*_i$ for $1\le i\le m$ and $\rho \in \mathbb{R}$, resulting in another formulation of LULUPAPI expressed as:

$$\min_{w,b,\xi,w^*,b^*,\xi_i^*} \frac{1}{2}\|w\|_2^2 + \frac{\gamma}{2}\|w^*\|_2^2 + \quad (3)$$

$$C\sum_{i=m+1}^{n}\pi_i\xi_i + \rho C^*\sum_{i=1}^{m}\pi_i\xi_i^* + C^*\sum_{i=1}^{m}(w^*\cdot z_i^* + b^*)$$

$$\text{s.t. } \forall\, 1\le i\le m \quad y_i(w\cdot z_i + b) \ge 1 - (w^*\cdot z_i^* + b^*) - \xi_i^*$$
$$\forall\, 1\le i\le m \quad w^*\cdot z_i^* + b^* \ge 0$$
$$\forall\, 1\le i\le m \quad \xi_i^* \ge 0$$
$$\forall\, m+1\le i\le n \quad y_i(w\cdot z_i + b) \ge 1 - \xi_i$$
$$\forall\, m+1\le i\le n \quad \xi_i \ge 0$$

Supervised learning systems applying this formulation may have interesting properties, such as performance that is lower bounded by SVM performance.

In yet another example LULUPAPI configuration, a supervised learning system can achieve a better transfer of the knowledge obtained in privileged information space to the decision space by considering the mixture of slacks a $\xi'_i=y_i(w^*\cdot z_i^*+b^*)+\rho\xi^*_i$ for $1\le i\le m$ and $\rho \in \mathbb{R}$, resulting in a third formulation of LULUPAPI expressed as:

$$\min_{w,b,\xi,w^*,b^*,\xi_i^*} \frac{1}{2}\|w\|_2^2 + \frac{\gamma}{2}\|w^*\|_2^2 + \quad (4)$$

$$C\sum_{i=m+1}^{n}\pi_i\xi_i + \rho C^*\sum_{i=1}^{m}\pi_i\xi_i^* + C^*\sum_{i=1}^{m}y_i(w^*\cdot z_i^* + b^*)$$

-continued
$$\text{s.t. } \forall\, 1\le i\le m \quad y_i(w\cdot z_i + b) \ge 1 - y_i(w^*\cdot z_i^* + b^*) - \xi_i^*$$
$$\forall\, 1\le i\le m \quad y_i(w^*\cdot z_i^* + b^*) \ge 0$$
$$\forall\, 1\le i\le m \quad \xi_i^* \ge 0$$
$$\forall\, m+1\le i\le n \quad y_i(w\cdot z_i + b) \ge 1 - \xi_i$$
$$\forall\, m+1\le i\le n \quad \xi_i \ge 0$$

Any of these LULUPAPI formulations may be implemented in the enhanced machine learning models described herein, for example.

Any of these LULUPAPI formulations may be optimized by the enhanced machine learning model to generate the decisional rule/model for use in assessing test data. For example, by Lagrange multipliers, the dual optimization of the second LULUPAPI formulation (3) can be written as:

$$\min_{\alpha,\beta} D(\alpha,\beta) = \quad (5)$$

$$\sum_{i=1}^{n}\alpha_i - \frac{1}{2}\sum_{i,j=1}^{n}\alpha_i\alpha_j y_i y_j K_{i,j} - \frac{1}{2\gamma}\sum_{i,j=1}^{n}(\alpha_i+\beta_i-C^*)(\alpha_j+\beta_j-C^*)K_{i,j}^*$$

$$\text{s.t. } \sum_{i=1}^{n} y_i\alpha_i = 0 \quad (6)$$

$$\sum_{i=1}^{m}(\alpha_i+\beta_i-C^*) = 0 \quad (7)$$

$$\forall\, m+1\le i\le n, 0\le \alpha_i\le \pi_i C \quad (8)$$

$$\forall\, 1\le i\le m, \rho\pi_i C^* \ge \alpha_i \ge 0, \beta_i \ge 0 \quad (9)$$

where $K_{i,j} \triangleq K(z_i, z_j)$ and $K^*_{i,j} \triangleq K^*(z^{*i}, z^*_j)$ are the kernel in the decision space and the correcting space, respectively, with the decision function expressed as:

$$f(z) = w\cdot z + b = \sum_{i=1}^{n} y_i\alpha_i K(z_i, z) + b \quad (10)$$

Figure 4:
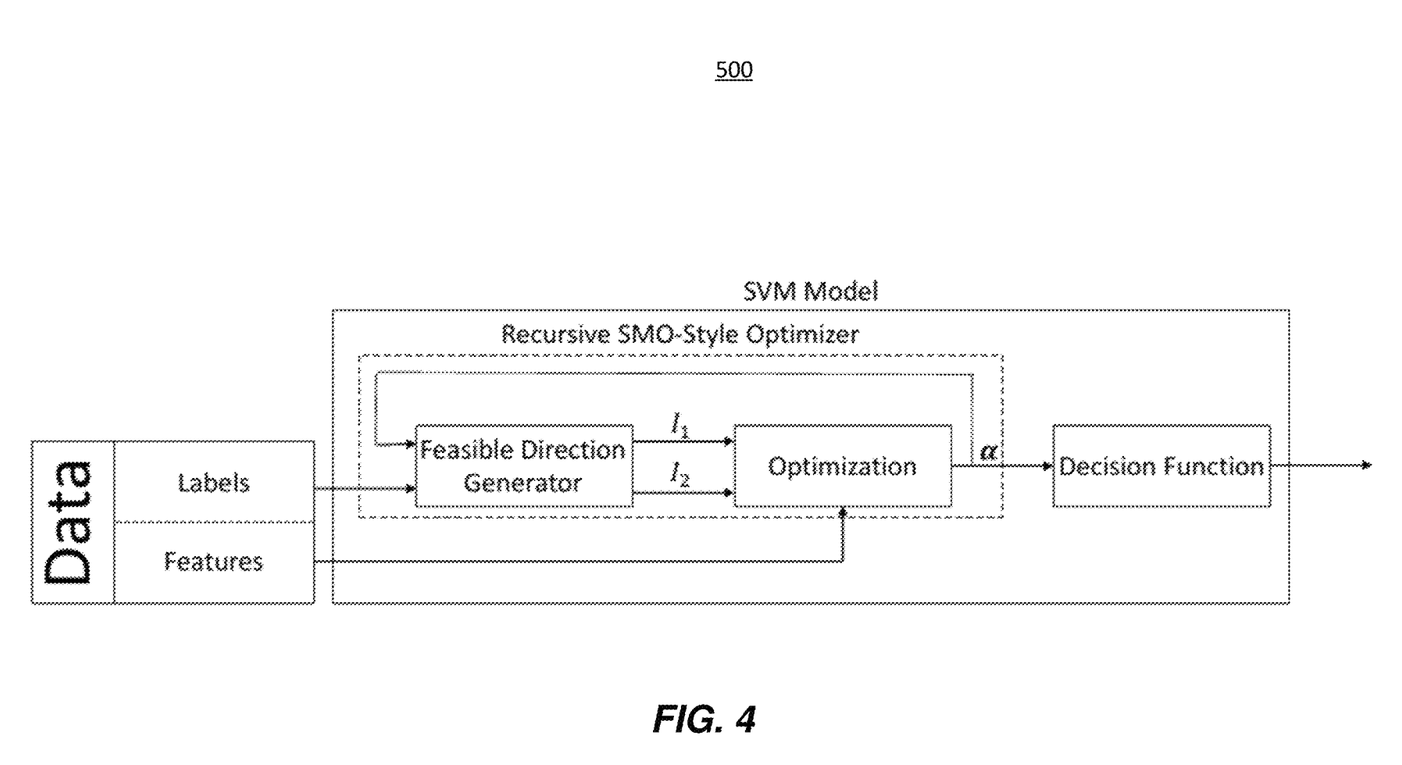
FIG. 4 illustrates a schematic of the machine learning model of FIG. 2 optimized in accordance with an example implementation of the techniques herein, in accordance with an example.

In an example, the LULUPAPI formulation is optimized using an SVM dual problem optimization process, such as a sequential minimal optimization (SMO) algorithm. FIG. 4 illustrates an example SMO optimizer implementation 500 of the system of FIG. 2, that is, of a conventional SVM supervised learning system. Data including labels and features are provided to an optimized SVM model that includes a recursive SMO optimizer and a resulting decision function.

As shown in the illustrated example, an iterative optimization process may be used to optimize the LULUPAPI formulation. The problem of equation (5) can be considered as the general form of the following expression:

$$\max_{\theta\in\mathcal{F}} D(\theta)$$

where $\theta \in \mathbb{R}^k$ and $D:\mathbb{R}^k \to \mathbb{R}$ is a concave quadratic function and $\mathcal{F}$ is a convex compact set of linear equalities and inequalities. At each iteration, a feasible direction generator determines the sets $I_t$ of maximally sparse feasible directions such that all the constraints (e.g., Equations 6, 7, 8, and 9) are satisfied. With the maximal sparse feasible directions determined from the label data, an optimizer receives feature data and optimizes these feasible directions, choosing the one that optimizes a cost function, which is then used as the starting point for the next iteration of the algorithm.

For example, an implementation of the recursive SMO optimizer, the supervised learning system starts the process by introducing the maximally feasible directions. The cost function in Equation (5) has n+m variables, i.e., $\{\alpha_i\}_{i=1}^n$ and $\{\beta_i\}_{i=1}^n$. These can be combined into a single (n+m)-variable vector $\theta$ by concatenating the $\alpha$ and $\beta$ variables: $\theta \triangleq (\alpha, \beta)^T$. Thus, each maximally sparse feasible direction is $\in \mathbb{R}^{n \cdot m}$. From this, it can be verified that in an example, Equation (5) has 9 sets of such directions as follows:

$$I_1 \triangleq \{u_s | s=(s_1,s_2), n+1 \le s_1, s_2 \le n+m, s_1 \ne s_2; u_{s_1}=1, u_{s_2}=-1, \theta_{s_1}>0, \forall i \in su_i=0\}. \quad 1)$$

$$I_2 \triangleq \{u_s | s=(s_1,s_2), 1 \le s_1, s_2 \le m, s_1 \ne s_2, y_{s_1}=y_{s_2}; u_{s_1}=1, \theta s_1 < \rho C^* \pi s_1, u_{s_2}=-1, \theta_{s_2}>0, \zeta i \in su_i=0\}. \quad 2)$$

$$I_3 \triangleq \{u_s | s=(s_1,s_2), m+1 \le s_1, s_2 \le n, s_1 \ne s_2, y_{s_1}=y_{s_2}; u_{s_1}=1, \theta_{s_1} < C \pi s_1, u_{s_2}=-1, \theta_{s_2}>0, \forall i \in su_i=0\}. \quad 3)$$

$$I_4 \triangleq \{u_s | s=(s_1,s_2), m+1 \le s_1, s_2 \le n, s_1 \ne s_2, y_{s_1} \ne y_{s_2}, \forall i \in su_i=0; u_{s_1}=u_{s_2}=1, \theta_{s_1} < C \pi s_1, \theta_{s_2} < C \pi s_2 \text{ or } u_{s_1}=u_{s_2}=-1, \theta_{s_1}>0, \theta_{s_2}>0\}. \quad 4)$$

$$I_5 \triangleq \{u_s | s=(s_1,s_2,s_3), 1 \le s_1, s_2 \le m, n-1 \le s_3 \le n+m, s_1 \ne s_2, y_{s_1} \ne y_{s_2}, \forall i \in su_i=0; u_{s_1}=u_{s_2}=1, \theta_{s_1} < \rho C^* \pi s_1, \theta_{s_2} < \rho C^* \pi s_2, u_{s_3}=-2, \theta_{s_3}>0 \text{ or } u_{s_1}=u_{s_2}=-1, \theta_{s_1}>0, \theta_{s_2}>0, u_{s_3}=2\}. \quad 5)$$

$$I_6 \triangleq \{u_s | s=(s_1,s_2,s_3), 1 \le s_1 \le m, m+1 \le s_2 \le n, n+1 \le s_3 \le n+m, y_{s_1}=y_{s_2}, \forall i \in su_i=0; u_{s_1}=1, \theta_{s_1} < \rho C^* \pi s_1, u_{s_2}=-1, \theta_{s_2} \ge 0, u_{s_3}=-1, \theta_{s_3} \ge 0 \text{ or } u_{s_1}=-1, \theta_{s_1} \ge 0, u_{s_2}=1, \theta_{s_2} < C \pi s_2, u_{s_3}=1\}. \quad 6)$$

$$I_7 \triangleq \{u_s | s=(s_1,s_2,s_3), 1 \le s_1 \le m, m+1 \le s_2 \le n, n+1 \le s_3 \le n+m, y_{s_1} \ne y_{s_2}, \forall i \in su_i=0; u_{s_1}=u_{s_2}=1, \theta_{s_1} < \rho C^* \pi s_1, \theta_{s_2} > C \pi s_2, u_{s_3}=1, \theta_{s_3}>0 \text{ or } u_{s_1}=u_{s_2}=-1, \theta_{s_1}>0, \theta_{s_2}>0, u_{s_3}=1\}. \quad 7)$$

$$I_8 \triangleq \{u_s | s=(s_1,s_2,s_3), 1 \le s_1, s_2 \le m, m+1 \le s_3 \le n, s_1 \ne s_2, y_{s_1} \ne y_{s_2}, y_{s_3}=y_{s_2}, \forall i \in su_i=0; u_{s_1}=1, \theta_{s_1} < \rho C^* \pi s_1, u_{s_2}=-1, \theta_{s_2}>0, u_{s_3}=2, \theta_{s_3} < C \pi s_3 \text{ or } u_{s_1}=-1, \theta_{s_1}>0, u_{s_2}=1, \theta_{s_2} < \rho C^* \pi s_2, u_{s_3}=-2, \theta_{s_2}>0\}. \quad 8)$$

$$I_9 \triangleq \{u_s | s=(s_1,s_2,s_3), 1 \le s_1, s_2 \le m, m+1 \le s_3 \le n, s_1 \ne s_2, y_{s_1} \ne y_{s_2}, y_{s_3}=y_{s_1}, \forall i \in su_i=0; u_{s_1}=1, \theta_{s_1} < \rho C^* \pi s_1, u_{s_2}=-1, \theta_{s_2}>0, u_{s_3}=-2, \theta_{s_3}<0 \text{ or } u_{s_1}=-1, \theta_{s_1}>0, u_{s_2}=1, \theta_{s_2} < \rho C^* \pi s_2, u_{s_3}=-2, \theta_{s_2} < C \pi s_3\}. \quad 9)$$

It can be verified that if we move from any feasible point $\theta^{old}$ in the direction of $u_s \in U I_i$, it satisfies the constraints corresponding to dual SVM problems. In this example, the optimization process finds $\theta = \theta^{old} + \lambda^*(s) u_s$, where $u_s$ and $\lambda^*(s)$ maximize the corresponding cost function, $D(\theta^{old} + \lambda u_s)$ such that the constraints are satisfied.

Figure 5:
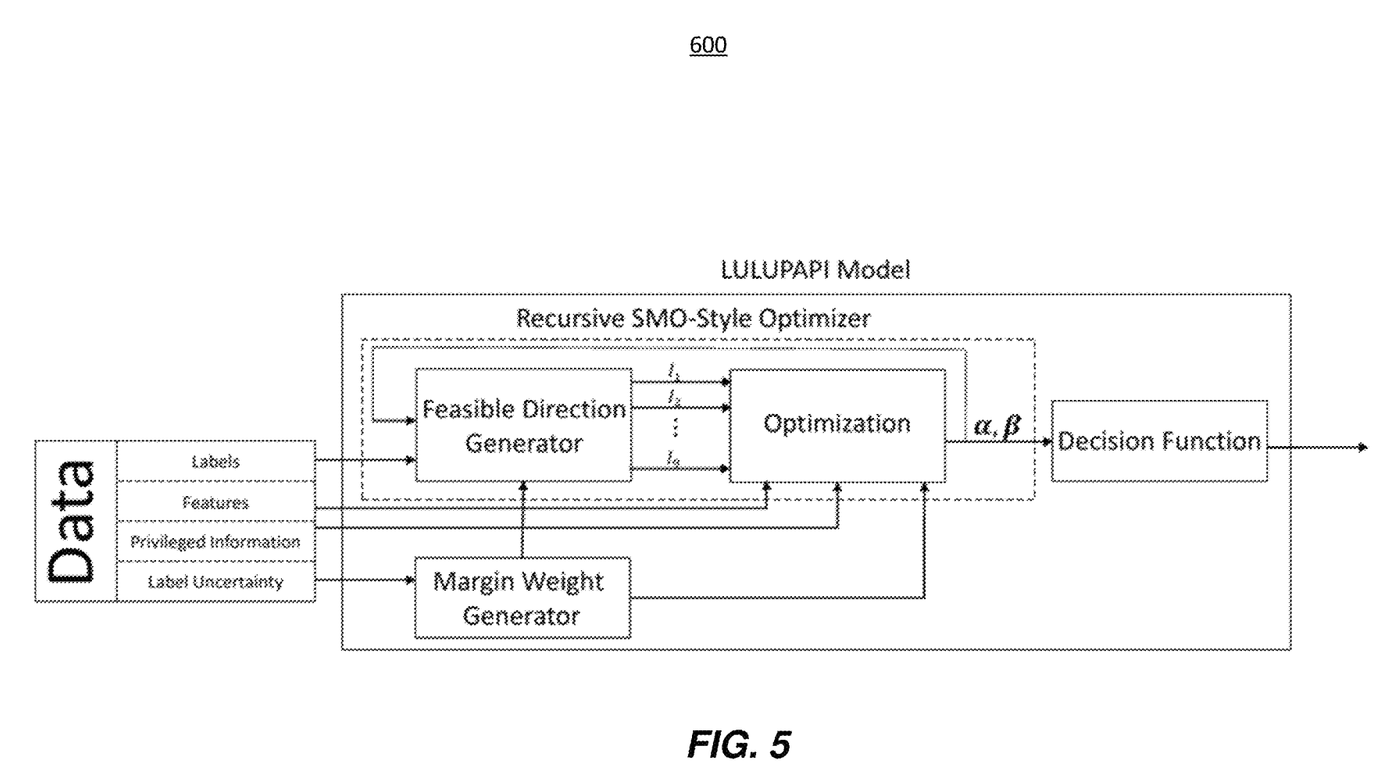
FIG. 5 illustrates a schematic of the machine learning model of FIG. 3 optimized in accordance with an example implementation of the techniques herein, in accordance with an example.

FIG. 5 illustrates an example supervised learning system 600 in accordance with the foregoing example, having an optimized LULUPAPI formulation, with similar features to that of FIG. 4. The supervised learning system of FIG. 5 is configured to optimize with privileged information and label uncertainty data. The privileged information is provided to the optimization process. The label uncertainty data is provided to a margin weight generator that converts measures of label uncertainty into weights that are used to determine the best margins within the optimization process. In the example depicted in FIG. 6, clinicians can report their level of confidence in their diagnosis, denoted by $l_i$, using a 1-8 scale, in which 1 is not ARDS with high confidence and 8 is ARDS with high confidence. A margin weight generator $\pi_i = (|l_i - p_1| - p_2) p_3 + p_4$, with $p_1 = 4.5$, $p_2 = 3$, $p_3 = 0.2$ and $p_4 = 0.9$, is then employed to scale the $l_i$s from the range 1-8 into the range 0.4-1 such that high-confidence cases $l_i = 1$ and $l_i = 8$ are mapped to $\pi_i = 1$ and low-confidence cases $l_i = 4$ and $l_i = 5$ are mapped to $\pi_i = 0.4$.

In various examples herein, supervised learning systems can provide numerous advantages over conventional systems. These include the ability to train on data with partially available privileged information. Supervised learning systems may be configured into different models (at least three shown above) such operation, and they may further implement SMO algorithms for each of these different models. Further, supervised learning systems can incorporate label uncertainty and integrate with privileged information. Further still, supervised learning systems demonstrate the viability of more maximally sparse feasible directions. That is, considering both training samples with privileged information and without privileged information adds flexibility in searching for maximally sparse feasible direction. In configurations like that of FIG. 4, for SVM model, there are only two possible maximally sparse feasible directions. And, for configurations like that of FIG. 5, for LULUPAPI formulations incorporating privileged information and label uncertainty data, there are many more such directions (nine in the illustrated example). In practice, this flexibility helps the recursive SMO-style optimizer to converge faster in configurations like that of FIG. 5 over that of FIG. 4.

Figure 6:
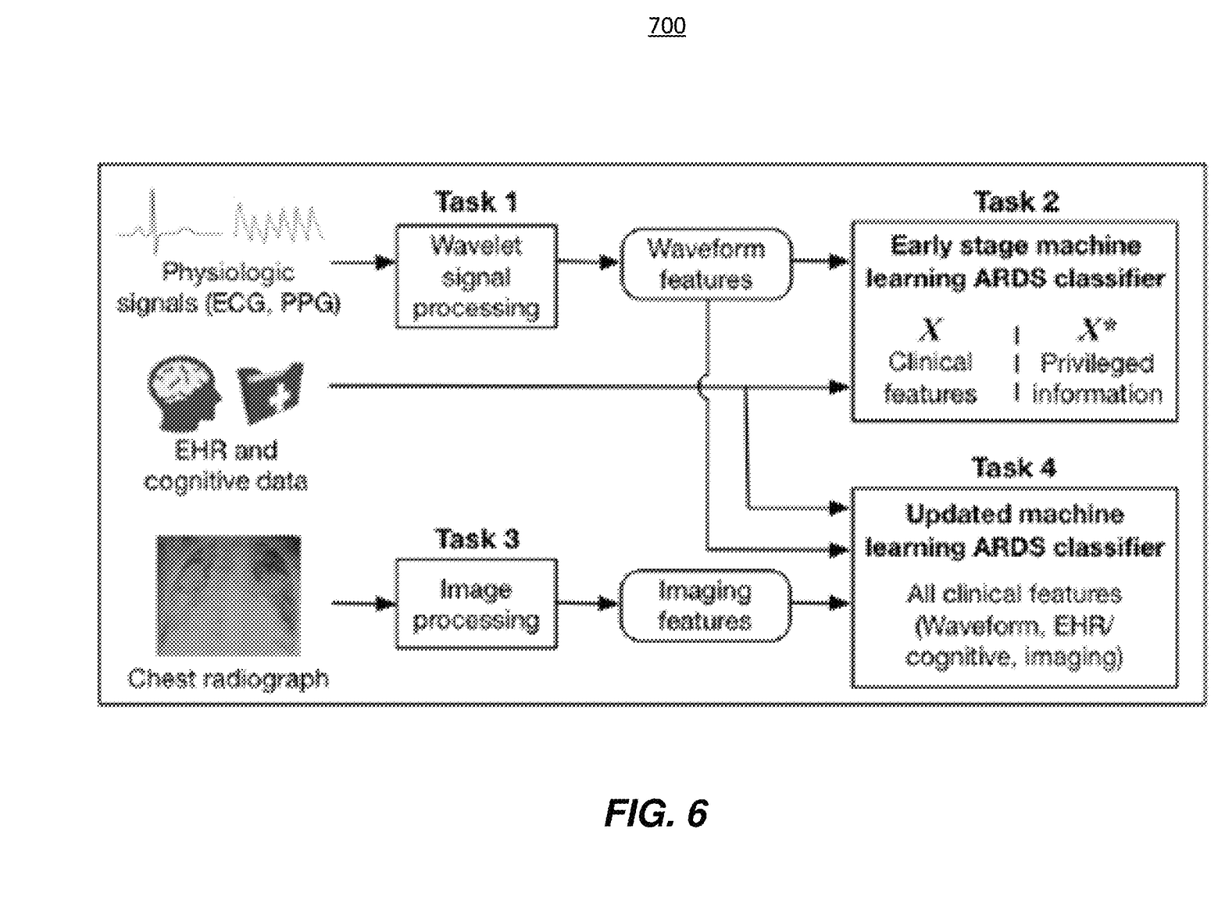
FIG. 6 illustrates an example ARDS analysis system implementing the framework of FIG. 5, in accordance with an example.

FIG. 6 illustrates an example ARDS analysis system 700 implementing a supervised learning system implementing techniques herein. The ARDS analysis system first receives physiologic data, such as electrocardiography (ECG) data, photoplethysmography (PPG) data, etc. taken for a patient. Initial signal processing is performed, such as wavelet signal processing that transform these received signals into waveform features. This initial signal processing may further include signal smoothing, amplitude normalizations, band pass filtering, and other preliminary processing processes. Furthermore, while wavelet signal processing is illustrated, other transformation processes may be used to identify constituent features.

The identified features data for the patient is provided to a first stage machine learning ARDS classifier that has been configured to implement a trained model of classifying ARDS based on received physiological data, in particular, waveform features obtained from the physiological data. In the illustrated example, the first stage machine learning ARDS is trained based on received clinical data, such as the physiological data, as well as privileged information such as electronic health record (EHR) data and cognitive data. FIG. 4 illustrates an example supervised learning system configuration for implementing the first stage machine learning ARDS for such configurations. In some examples, the first stage machine learning ARDS applies a trained model classifying ARDS based on received clinical data, privileged information, and in some examples uncertain labeled privileged information. FIG. 5 illustrates an example supervised learning system configuration for such configurations.

The ARDS analysis system is also configured to analyze medical image data, in this example, chest radiographs. Initial image processing is performed on the medical image data to identify imaging features, such as summary statistics derived from pixel intensity histograms (including mean, variance, skewness, and kurtosis), for example, using noise filtering, edge detection, segmentation processes. These imaging features are combined with the waveform features, privileged information, including uncertain label data, to develop an updated machine learning ARDS classifier, for example implementing the configurations of FIG. 5.

In an example initial wavelet signal processing for filtering and feature extraction from ECG and PPG signals, the ARDS system of FIG. 6 uses a signal processing method based on a packet-based extension of Dual Tree Complex Wavelet Transform (DTCWT), called M-band Dual Tree Complex Wavelet Packet Transform (DTCWPT). To construct a packet form of the M-band DTCWPT, in an example, the wavelet signal processor repeatedly decomposes each of the sub-bands using low-pass/high-pass, using reconstruction filter banks, so that the response of each branch of the wavelet packet filter bank is the discrete Hilbert transform of the corresponding branch of the first wavelet packet filter bank. The use of M-band decomposition in the packet transform provides a dictionary of bases over which one can search for an optimal representation of a given signal. Moreover, an advantage of the wavelet packet approach to DTCWT (i.e., M-band DTCWPT) is its ability to automatically select the proper wavelets with a suitable match with the present frequencies in the signal.

After feature selection, the wavelet signal processor selected the top features (mainly wavelet-based features) to develop models to assess and predict subjects' levels of hemodynamic instability (modeled using lower body negative pressure, a human model of hypovolemia). In any example, we used the wavelet signal processor to extract an average of 12 feature windows at a window size of 120 beats for a patient sample. We compared those against traditional heart rate variability (HRV) features (i.e., standard features based on the poser signal in multiple frequency bands), and our features described in this study were used separately for developing independent models. The classification models developed (i.e., the machine learning ARDS classifier) with our identified features outperformed typical HRV features in terms of Area under the Curve (AUC) and accuracy across all window sizes in a receiver operating curves (ROC) analysis. Moreover, the classification model for our identified features (120-beats window) outperformed the best model for the typical HRV features (180 beats window) in terms of AUC and accuracy by 0.05 and 5.37%, respectively, in an example.

As shown, the present techniques provide novel computational methodologies capable of synthesizing and integrating longitudinal electronic health data streams for real-time and continuous health status monitoring and early detection of disease. In an example, these techniques are used to address the problem of monitoring patients with lung disease to detect the presence of the ARDS at early stages. The techniques combine capabilities of machine learning, privileged learning and learning from uncertain data, in an optimized manner. While examples are described herein in reference to diagnosis of ARDS, the proposed techniques may be used across healthcare settings, allowing for better characterization of patient health status in both in-hospital and in-home settings via portable electronic monitoring devices.

Figure 7:
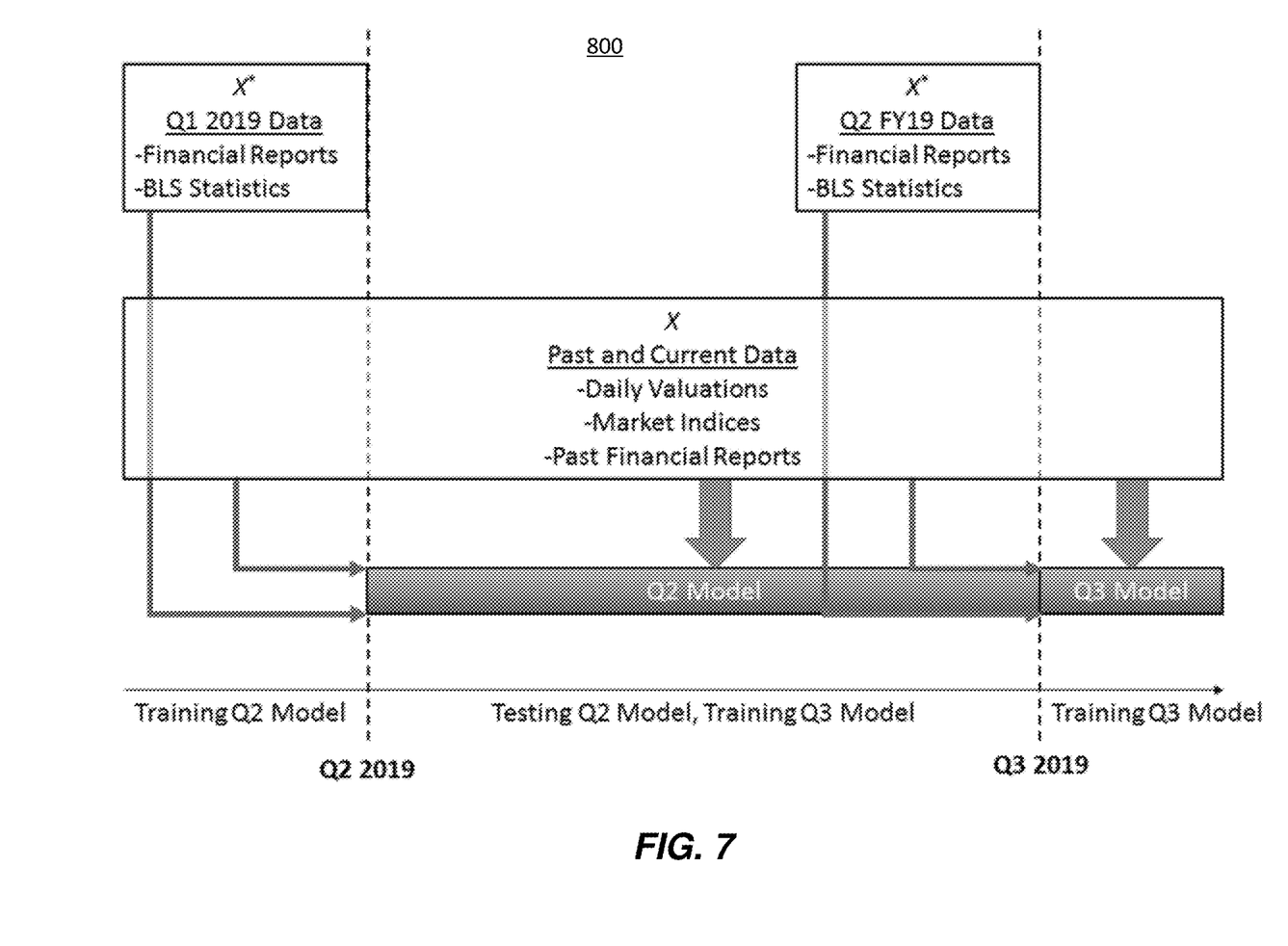
FIG. 7 illustrates an example earnings forecasting system implementing the framework of FIG. 5, in accordance with an example.

FIG. 7 illustrates an example earnings forecasting system 800 implementing a supervised learning system implementing techniques herein. The earnings forecasting system can be used to forecast if a particular company will achieve a positive or negative net income in the next quarter. In the training phase, the system utilizes two datasets X and X* as input into the machine learning model. Dataset X can include any past financial data, current market index values, and current stock valuations related to the company or its associated industry. Data contained in X should be available during both the training of the model and its use in production, i.e., for forecasting net income given current market conditions. Dataset X* contains privileged information in the form of BLS (Bureau of Labor Statistics) statistics such as the Employment Cost index and the most recent financial quarterly report that will not be available until the next quarter. In this example, the quarterly report and BLS statistics available at the end of Q1 2019 are used as privileged information to train an earnings forecasting system, the Q2 Model, for using throughout Q2 2019. The Q2 model will only use the information available within dataset X to generate its forecasts. Once the Q2 2019 financial quarterly reports and new BLS statistics become available, a new model is trained to forecast net income for Q3 2019, the Q3 model. This process can be repeated for any subsequent quarter.

Throughout this specification, plural instances may implement components, operations, or structures described as a single instance. Although individual operations of one or more methods are illustrated and described as separate operations, one or more of the individual operations may be performed concurrently, and nothing requires that the operations be performed in the order illustrated. Structures and functionality presented as separate components in example configurations may be implemented as a combined structure or component. Similarly, structures and functionality presented as a single component may be implemented as separate components. These and other variations, modifications, additions, and improvements fall within the scope of the subject matter herein.

Additionally, certain embodiments are described herein as including logic or a number of routines, subroutines, applications, or instructions. These may constitute either software (e.g., code embodied on a non-transitory, machine-readable medium) or hardware. In hardware, the routines, etc., are tangible units capable of performing certain operations and may be configured or arranged in a certain manner. In example embodiments, one or more computer systems (e.g., a standalone, client or server computer system) or one or more hardware modules of a computer system (e.g., a processor or a group of processors) may be configured by software (e.g., an application or application portion) as a hardware module that operates to perform certain operations as described herein.

In various embodiments, a hardware module may be implemented mechanically or electronically. For example, a hardware module may comprise dedicated circuitry or logic that is permanently configured (e.g., as a special-purpose processor, such as a field programmable gate array (FPGA) or an application-specific integrated circuit (ASIC)) to perform certain operations. A hardware module may also comprise programmable logic or circuitry (e.g., as encompassed within a general-purpose processor or other programmable processor) that is temporarily configured by software to perform certain operations. It will be appreciated that the decision to implement a hardware module mechanically, in dedicated and permanently configured circuitry, or in temporarily configured circuitry (e.g., configured by software) may be driven by cost and time considerations.

Accordingly, the term "hardware module" should be understood to encompass a tangible entity, be that an entity that is physically constructed, permanently configured (e.g., hardwired), or temporarily configured (e.g., programmed) to operate in a certain manner or to perform certain operations described herein. Considering embodiments in which hardware modules are temporarily configured (e.g., programmed), each of the hardware modules need not be configured or instantiated at any one instance in time. For example, where the hardware modules comprise a general-purpose processor configured using software, the general-purpose processor may be configured as respective different hardware modules at different times. Software may accordingly configure a processor, for example, to constitute a particular hardware module at one instance of time and to constitute a different hardware module at a different instance of time.

Hardware modules can provide information to, and receive information from, other hardware modules. Accordingly, the described hardware modules may be regarded as being communicatively coupled. Where multiple of such hardware modules exist contemporaneously, communications may be achieved through signal transmission (e.g., over appropriate circuits and buses) that connect the hardware modules. In embodiments in which multiple hardware modules are configured or instantiated at different times, communications between such hardware modules may be achieved, for example, through the storage and retrieval of information in memory structures to which the multiple hardware modules have access. For example, one hardware module may perform an operation and store the output of that operation in a memory device to which it is communicatively coupled. A further hardware module may then, at a later time, access the memory device to retrieve and process the stored output. Hardware modules may also initiate communications with input or output devices, and can operate on a resource (e.g., a collection of information).

The various operations of example methods described herein may be performed, at least partially, by one or more processors that are temporarily configured (e.g., by software) or permanently configured to perform the relevant operations. Whether temporarily or permanently configured, such processors may constitute processor-implemented modules that operate to perform one or more operations or functions. The modules referred to herein may, in some example embodiments, comprise processor-implemented modules.

Similarly, the methods or routines described herein may be at least partially processor-implemented. For example, at least some of the operations of a method may be performed by one or more processors or processor-implemented hardware modules. The performance of certain of the operations may be distributed among the one or more processors, not only residing within a single machine, but deployed across a number of machines. In some example embodiments, the processor or processors may be located in a single location (e.g., within a home environment, an office environment or as a server farm), while in other embodiments the processors may be distributed across a number of locations.

The performance of certain of the operations may be distributed among the one or more processors, not only residing within a single machine, but deployed across a number of machines. In some example embodiments, the one or more processors or processor-implemented modules may be located in a single geographic location (e.g., within a home environment, an office environment, or a server farm). In other example embodiments, the one or more processors or processor-implemented modules may be distributed across a number of geographic locations.

Unless specifically stated otherwise, discussions herein using words such as "processing," "computing," "calculating," "determining," "presenting," "displaying," or the like may refer to actions or processes of a machine (e.g., a computer) that manipulates or transforms data represented as physical (e.g., electronic, magnetic, or optical) quantities within one or more memories (e.g., volatile memory, non-volatile memory, or a combination thereof), registers, or other machine components that receive, store, transmit, or display information.

As used herein any reference to "one embodiment" or "an embodiment" means that a particular element, feature, structure, or characteristic described in connection with the embodiment is included in at least one embodiment. The appearances of the phrase "in one embodiment" in various places in the specification are not necessarily all referring to the same embodiment.

Some embodiments may be described using the expression "coupled" and "connected" along with their derivatives. For example, some embodiments may be described using the term "coupled" to indicate that two or more elements are in direct physical or electrical contact. The term "coupled," however, may also mean that two or more elements are not in direct contact with each other, but yet still co-operate or interact with each other. The embodiments are not limited in this context.

Those skilled in the art will recognize that a wide variety of modifications, alterations, and combinations can be made with respect to the above described embodiments without departing from the scope of the invention, and that such modifications, alterations, and combinations are to be viewed as being within the ambit of the inventive concept.

While the present invention has been described with reference to specific examples, which are intended to be illustrative only and not to be limiting of the invention, it will be apparent to those of ordinary skill in the art that changes, additions and/or deletions may be made to the disclosed embodiments without departing from the spirit and scope of the invention.

The foregoing description is given for clearness of understanding; and no unnecessary limitations should be understood therefrom, as modifications within the scope of the invention may be apparent to those having ordinary skill in the art.

What is claimed:

1. A computer-implemented method of developing a classifier model for identifying a medical condition of a subject, the method comprising:

receiving training data for a plurality of subjects, where the training data includes sensed physiological data, imaging data, demographic data, and/or other clinical data, where at least some of the training data is for subjects having the medical condition and at least some of the training data is for subjects not having the medical condition, wherein the training data includes privileged information where at least a portion of the privileged information is label uncertain privileged information;

identifying the label uncertain privileged information;

applying a penalty parameter to each label uncertain privileged information, wherein the penalty parameter establishes a soft-margin decisional boundary for the label uncertain privileged information;

performing an optimization on (i) the label uncertain privileged information having the penalty parameters, (ii) the privileged information in the training data that has certain labels, and (iii) non-privileged information in training data, to develop a mapping to an outcome determination of the medical condition; and generating a classifier model based on the mapping to classify testing data as corresponding to the presence of the medical condition or to the absence of the medical condition.

2. The computer-implemented method of claim 1, further comprising:
applying the training data to a support vector machine (SVM) framework configured to map training data to a vector space and generate a decision hyperplane classifier model for identifying the presence of the medical condition and for identifying the absence of the medical condition.

3. The computer-implemented method of claim 2, further comprising:
configuring the support vector machine (SVM) framework to map privileged information in the training data and non-privileged information in the training data to the vector space for generating the decision hyperplane classifier model.

4. The computer-implemented method of claim 2, wherein the training data is expressed as:

$$(x_1, x^*_1, y_1, \pi_1), \ldots, (x_m, x^*_m, y_m, \pi_m), (x_{m+1}, y_{m+1}, \pi_{m+1}), (x_{m+2}, y_{m+2}, \pi_{m+2}), \ldots, (x_n, y_n, \pi_n)$$

$$x_i \in X, x^*_i \in X^*, y_i \in \{-1, 1\}, \pi_i \in \mathbb{R}$$

5. The computer-implemented method of claim 4, further comprising:
applying the penalty parameter by performing a correction function for identifying hyperplane parameters; and
generating the classifier model by simultaneous optimization of the following expression:

$$\min_{w, b, w^*, b^*, \xi} \frac{1}{2}\|w\|_2^2 + \frac{\gamma}{2}\|w^*\|_2^2 + C \sum_{i=m+1}^{n} \pi_i \xi_i + C^* \sum_{i=1}^{m} (w^* \cdot z^*_i + b^*) \quad (2)$$

s.t. $\forall\, 1 \leq i \leq m \quad y_i(w \cdot z_i + b) \geq 1 - (w^* \cdot z^*_i + b^*)$
$\forall\, 1 \leq i \leq m \quad w^* \cdot z^*_i + b^* \geq 0$
$\forall\, m+1 \leq i \leq n \quad y_i(w \cdot z_i + b) \geq 1 - \xi_i$
$\forall\, m+1 \leq i \leq n \quad \xi_i \geq 0.$ 6. The computer-implemented method of claim 4, further comprising:
applying the penalty parameter by performing a correction function for identifying hyperplane parameters; and
generating the classifier model by simultaneous optimization of the following expression:

$$\min_{w, b, \xi, w^*, b^*, \xi^*_i} \frac{1}{2}\|w\|_2^2 + \frac{\gamma}{2}\|w^*\|_2^2 + \quad (3)$$

$$C \sum_{i=m+1}^{n} \pi_i \xi_i + \rho C^* \sum_{i=1}^{m} \pi_i \xi^*_i + C^* \sum_{i=1}^{m} (w^* \cdot z^*_i + b^*)$$

s.t. $\forall\, 1 \leq i \leq m \quad y_i(w \cdot z_i + b) \geq 1 - (w^* \cdot z^*_i + b^*) - \xi^*_i$
$\forall\, 1 \leq i \leq m \quad w^* \cdot z^*_i + b^* \geq 0$
$\forall\, 1 \leq i \leq m \quad \xi^*_i \geq 0$
$\forall\, m+1 \leq i \leq n \quad y_i(w \cdot z_i + b) \geq 1 - \xi_i$
$\forall\, m+1 \leq i \leq n \quad \xi_i \geq 0.$ 7. The computer-implemented method of claim 4, further comprising:
applying the penalty parameter by performing a correction function for identifying hyperplane parameters; and
generating the classifier model by simultaneous optimization of the following expression:

$$\min_{w, b, \xi, w^*, b^*, \xi^*_i} \frac{1}{2}\|w\|_2^2 + \frac{\gamma}{2}\|w^*\|_2^2 + \quad (4)$$

$$C \sum_{i=m+1}^{n} \pi_i \xi_i + \rho C^* \sum_{i=1}^{m} \pi_i \xi^*_i + C^* \sum_{i=1}^{m} y_i(w^* \cdot z^*_i + b^*)$$

s.t. $\forall\, 1 \leq i \leq m \quad y_i(w \cdot z_i + b) \geq 1 - y_i(w^* \cdot z^*_i + b^*) - \xi^*_i$
$\forall\, 1 \leq i \leq m \quad y_i(w^* \cdot z^*_i + b^*) \geq 0$
$\forall\, 1 \leq i \leq m \quad \xi^*_i \geq 0$
$\forall\, m+1 \leq i \leq n \quad y_i(w \cdot z_i + b) \geq 1 - \xi_i$
$\forall\, m+1 \leq i \leq n \quad \xi_i \geq 0.$ 8. The computer-implemented method of claim 1, further comprising performing the optimization by applying a sequential minimal optimization to (i) the label uncertain privileged information having the penalty parameters, (ii) the privileged information in the training data that has certain labels, and (iii) non-privileged information in training data, to develop a mapping to an outcome determination of the medical condition.

9. The computer-implemented method of claim 1, wherein the medical condition is acute respiratory distress syndrome.

10. The computer-implemented method of claim 8, wherein the physiological data comprises continuous electrocardiogram (ECG) and/or photoplethysmography (PPG) data.

11. The computer-implemented method of claim 8, wherein the image data comprises: chest x-ray image data.

* * * * *